United States Patent
Jin et al.

(10) Patent No.: US 11,041,857 B2
(45) Date of Patent: Jun. 22, 2021

(54) METHOD FOR PREPARING UPCONVERSION-LUMINESCENCE FLEXIBLE HYBRID MEMBRANE FOR VISUAL DETECTION OF TUMOR MARKER

(71) Applicant: QINGDAO UNIVERSITY, Qingdao (CN)

(72) Inventors: Hui Jin, Qingdao (CN); Rijun Gui, Qingdao (CN); Yujiao Sun, Qingdao (CN); Xiaowen Jiang, Qingdao (CN)

(73) Assignee: QINGDAO UNIVERSITY, Qingdao (CN)

( * ) Notice: Subject to any disclaimer, the term of this patent is extended or adjusted under 35 U.S.C. 154(b) by 0 days.

(21) Appl. No.: 17/044,495

(22) PCT Filed: Apr. 3, 2019

(86) PCT No.: PCT/CN2019/081160
§ 371 (c)(1),
(2) Date: Oct. 1, 2020

(87) PCT Pub. No.: WO2020/191797
PCT Pub. Date: Oct. 1, 2020

(65) Prior Publication Data
US 2021/0041433 A1  Feb. 11, 2021

(30) Foreign Application Priority Data
Mar. 25, 2019  (CN) .......................... 201910226383.7

(51) Int. Cl.
*G01N 33/543* (2006.01)
*G01N 33/574* (2006.01)

(52) U.S. Cl.
CPC .............. *G01N 33/54393* (2013.01); *G01N 33/54306* (2013.01); *G01N 33/57484* (2013.01)

(58) Field of Classification Search
CPC .................. G01N 33/54393; G01N 33/54306
See application file for complete search history.

(56) References Cited

U.S. PATENT DOCUMENTS

2008/0085088 A1   4/2008  Lin et al.

FOREIGN PATENT DOCUMENTS

| CN | 1267566 C | 8/2006 |
|---|---|---|
| CN | 101812528 A | 8/2010 |
| CN | 102832267 A | 12/2012 |
| CN | 105063889 A | 11/2015 |
| CN | 105572092 A | 5/2016 |
| CN | 107043093 A * | 8/2017 |
| CN | 107748147 A | 3/2018 |
| CN | 109432422 A * | 3/2019 |

OTHER PUBLICATIONS

Wikipedia entry for "Electron acceptor", retrieved from https://en.wikipedia.org/wiki/Electron_acceptor on Jan. 9, 2021, 2 pages (Year: 2021).*
Li et al. "High-Throughput Signal-On Photoelectrochemical Immunoassay of Lysozyme Based on Hole-Trapping Triggered by Disintegrating Bioconjugates of Dopamine-Grafted Silica Nanospheres" ACS Sens. 2018, 3, 1480-1488 (Year: 2018).*
Heřmánková et al. "Redox properties of individual quercetin moieties" Free Radical Biology and Medicine 143 (2019) 240-251, https://doi.org/10.1016/j.freeradbiomed.2019.08.001 (Year: 2019).*
Gui et al. "Black phosphorus quantum dots: synthesis, properties, functionalized modification and applications" Chem. Soc. Rev., 2018, 47, 6795, DOI: 10.1039/c8cs00387d (Year: 2018).*
Zhang et al. "Black Phosphorus Quantum Dots", Angew. Chem. Int. Ed. 2015, 54, 3653-3657, DOI: 10.1002/anie.201409400 (Year : 2015).*
Hui Jin et al., Two-photon excited quantum dots with compact surface coatings of polymer ligands used as an upconversion luminescent probe for dopamine detection in biological fluids, Analyst, 2015, pp. 2037-2043, 140.
Hui Jin et al., Ratiometric two-photon excited photoluminescence of quantum dots triggered by near-infrared-light for real-time detection of nitric oxide release in situ, Analytica Chimica Acta, 2016, pp. 48-54, 922.

* cited by examiner

*Primary Examiner* — Christine Foster
(74) *Attorney, Agent, or Firm* — Bayramoglu Law Offices LLC

(57) ABSTRACT

A method for preparing an upconversion-luminescence flexible hybrid membrane for visual detection of tumor markers is provided. Metal ion doped black phosphorus quantum dots (M-BPQDs) are prepared by adopting ultrasonic and solvothermal processes; mesoporous $SiO_2$ grows on the surfaces of the M-BPQDs and amination modification is performed; the M-BPQDs are connected with carboxylated single-stranded DNA1; receptor molecules enter pores; single-stranded DNA2 aptamers and the DNA1 are combined due to base complementation to encapsulate receptors in the pores; and an M-BPQDs probe is prepared. DNA1 terminal-SH and a composite membrane are formed by assembling polymethyl methacrylate-polyimide-gold nanoparticles in a layer-by-layer manner bound by Au—S bonds, and the membrane and the probe are connected to construct the flexible hybrid membrane. The new flexible hybrid membrane is simple and inexpensive to prepare and is highly sensitive.

15 Claims, 2 Drawing Sheets

US 11,041,857 B2

METHOD FOR PREPARING UPCONVERSION-LUMINESCENCE FLEXIBLE HYBRID MEMBRANE FOR VISUAL DETECTION OF TUMOR MARKER

CROSS REFERENCE TO THE RELATED APPLICATIONS

This application is the national phase entry of International Application No. PCT/CN2019/081160, filed on Apr. 3, 2019, which is based upon and claims priority to Chinese Patent Application No. 201910226383.7, filed on Mar. 25, 2019, the entire contents of which are incorporated herein by reference.

TECHNICAL FIELD

The present invention belongs to the technical field of preparation of flexible hybrid membrane materials and visual detection probes, and more particularly, relates to a method for preparing an upconversion-luminescence flexible hybrid membrane for visual detection of tumor markers, and the flexible hybrid membrane prepared thereby can be used for the visual detection of upconversion luminescence of tumor markers in biological fluid samples.

BACKGROUND

In recent years, upconversion luminescence of quantum dots has attracted extensive interest and research. Quantum dots have a high two-photon absorption capacity and exhibit strong anti-Stokes emission, i.e., upconversion luminescence or two-photon fluorescence. In the field of biological and medical applications, the upconversion luminescence of quantum dots is significantly superior to conventional down-conversion fluorescence. The excitation wavelength of upconversion luminescence (such as near-infrared light, which has low energy but strong penetrating power) is greater than the emission wavelength thereof (such as visible light, which has high energy but weak penetrating power). This feature can help avoid the interference of biological autofluorescence and background fluorescence, thus improving the sensitivity and resolution of upconversion luminescence detection and imaging analysis. The upconversion luminescence of quantum dots has broad application prospects in the fields of deep tissue imaging, biochemical analysis, photodynamic therapy and energy conversion of cells and living bodies. Especially in the field of biomedicine, the upconversion luminescence of quantum dots will gradually replace the conventional down-conversion fluorescence, and develop into a more efficient photoluminescence analysis method.

Currently, tumor marker detection technologies mainly include two major categories: immunoassays and biosensors. Immunoassay involves an enzyme-linked immunosorbent assay, which has disadvantages such as high detection cost, complicated operation, and specific dye labeling. In recent years, researchers have developed different types of optical and electrochemical biosensors, but the development of simple, rapid and efficient methods for detecting tumor markers in clinical practice remains a challenge. The present invention utilizes the unique advantages of visible region upconversion luminescence in nano-bioanalysis, uses near-infrared light to excite quantum dots to generate visible region upconversion luminescence, realizes visual detection of target objects based on upconversion illuminating color gradation, and constructs a novel upconversion-luminescence flexible hybrid membrane to achieve simple, accurate, rapid, highly sensitive, quantitative and visual detection of tumor markers. The disclosed method for detecting tumor markers has broad application prospects in key technical fields such as early diagnosis of tumors, bio-imaging, and medical device development.

ZHANG Qunshe et al. disclosed a method for preparing crystalline silicon containing upconverted luminescent quantum dots (Invention Patent Publication No. CN102832267A); LI Jiasu et al. inserted rare earth ion doped upconversion-luminescence nanoparticles into polystyrene fibers to prepare a composite fiber felt thin film (Invention Patent Publication No. CN105063889A); DENG Shengsong et al. designed a white light-emitting upconverting nanoparticle and a test strip for simultaneous detection of multi-component tumor markers (Invention Patent Publication No. CN107748147A); Jin et al. reported quantum dot-based upconversion-luminescence probes for the detection of dopamine in biological fluids (Hui Jin, Rijun Gui, Zonghua Wang, et al. Two-photon excited quantum dots with compact surface coatings of polymer ligands used as an upconversion-luminescence probe for dopamine detection in biological fluids. *Analyst*, 140, 2037 (2015)); Jin et al. prepared a double quantum dot-based probe for ratiometric upconversion luminescence detection of nitric oxide (Hui Jin, Rijun Gui, Jie Sun, et al., Ratiometric two-photon excited photoluminescence of quantum dots triggered by near-infrared-light for real-time detection of nitric oxide release in situ. *Anal. Chim. Acta*, 922, 48 (2016)).

Although previous studies have involved the use of quantum dots and rare earth ion doped nanoparticle upconversion luminescence probes for chemical and biological detection, and the construction of upconversion-luminescence films based on rare earth ion doped nanoparticles, until now, there has been no reported use of upconversion based luminescence quantum dots constructed flexible hybrid membranes for visual detection of tumor markers in domestic and foreign literature and patents. The present invention designs a novel metal ion doped black phosphorus quantum dot upconversion-luminescence probe; when combining it with a flexible substrate to construct a flexible hybrid membrane and adding a trace amount of a biological fluid sample dropwise to the surface of the hybrid membrane to excite in the near infrared light, the tumor marker in the sample initiates a regular change in the intensity of upconversion luminescence of the probe, and the visual detection of the tumor marker is realized.

SUMMARY

The present invention aims to overcome the defects of the prior art described above, and to design an upconversion-luminescence flexible hybrid membrane for visual detection of tumor markers that is highly sensitive, inexpensive to produce, and simple to employ.

To achieve the above purpose, the present invention provides a method for preparing an upconversion-luminescence flexible hybrid membrane for visual detection of tumor markers, including the following steps:

(1) grinding block black phosphorus crystal into a powder, adding the powder to a polar solvent in which metal salt is dissolved, ultrasonically stripping black phosphorus nanosheets by a probe and a bath, adding a thiol ligand, and preparing metal ion doped black phosphorus quantum dots (M-BPQDs) by ultrasonic-assisted solvothermal treatment;

(2) growing mesoporous silica (mSiO$_2$) on the surfaces of M-BPQDs according to the Stöber method, conducting amination (—NH$_2$) modification to prepare M-BPQDs/mSiO$_2$—NH$_2$, and binding the M-BPQDs/mSiO$_2$—NH$_2$ to single-stranded DNA1 (HS-DNA1-COOH) by carboxy-amine coupling to prepare M-BPQDs/mSiO$_2$@DNA1;

(3) allowing an electron receptor molecule to enter a pore of mSiO$_2$ to complete the loading of the receptor molecule, adding specific aptamer single-stranded DNA2 for complementary base pairing with the DNA1 to form a double helix structure, and encapsulating the receptor molecule to obtain a nano-hybrid carrier probe M-BPQDs/mSiO$_2$@DNA1-DNA2@receptor;

(4) using polymethyl methacrylate (PMMA) as a layered substrate, bonding a layer of polyimide (PI) on the surface thereof, and immersing an electrode clip fixed PMAA-PI film in an electrolyte; using a KCl saturated calomel electrode as a reference electrode, a platinum wire electrode as an auxiliary electrode, and the PMMA-PI film as a working electrode, adding HAuCl$_4$ to the electrolyte, scanning by cyclic voltammetry, and electrochemically reducing the surface of the film to form gold nanoparticles (AuNPs) to prepare a PMMA-PI-AuNPs composite film; and (5) bonding DNA1 (HS-DNA1-COOH) terminal-SH on the probe and the AuNPs on the film by Au—S bond, and connecting the film and the probe together to construct a flexible hybrid membrane, where when a biological fluid sample contains a tumor marker, the sample is dropped onto the hybrid membrane, and an upconversion luminescence color change of the infiltrated hybrid membrane is observed under near-infrared light excitation to realize visual detection of the tumor marker.

The metal ion in step (1) is Ag$^+$, Mn$^{2+}$, Co$^{2+}$, Ni$^{2+}$, etc., and the M-BPQDs are 1-5 nm in size.

The surface of the mSiO$_2$ in step (2) is 50-200 nm in thickness.

The receptor in step (3) is 5-fluorouracil, dopamine, rutin, quercetin, etc., and the DNA2 is a single-stranded DNA aptamer of such markers as carcinoembryonic antigen (CEA), alpha-fetoprotein (AFP), carbohydrate antigen (CA), and prostate specific antigen (PSA).

In step (4), the PMMA is 50-100 nm in thickness, the PI is 1-2 μm in thickness, and the AuNPs are 10-100 nm in thickness.

In step (5), an upconversion luminescence emission peak has a wavelength of 500-600 nm, and the tumor marker has a concentration of 1 nM to 1 mM.

In the present invention, with thiol as a stabilizer, novel metal ion doped black phosphorus quantum dots (M-BPQDs) are prepared by adopting ultrasonic and solvothermal processes; mesoporous SiO$_2$ grows on the surfaces of the M-BPQDs and amination modification is performed; the M-BPQDs are connected with carboxylated single-stranded DNA1; receptor molecules enter pores; single-stranded DNA2 aptamers and the DNA1 are combined due to base complementation to encapsulate receptors in the pores, and a nano-carrier probe based on M-BPQDs is prepared. On the polymethyl methacrylate-polyimide-gold nanoparticles (PMMA-PI-AuNPs) composite film assembled with the other end of the DNA1-SH, the AuNPs are bonded by the Au—S bond to connect the film with the probe together to construct a flexible hybrid film. DNA2 is a single-stranded aptamer of a specific tumor marker. When the marker is contained in a biological fluid sample, a trace amount of the sample is added dropwise to the surface of the hybrid membrane, and the marker specifically binds to DNA2 to cause DNA2 to competitively break away from DNA1. This causes the release of receptors from the pores of the carrier. The receptors are far from M-BPQDs, and photoinduced electron transfer thereof is inhibited. Under the excitation of near-infrared light, the up-conversion luminescence of the visible region of M-BPQDs gradually recovers with the increase of the concentration of the marker, realizing the purpose of visual detection of up-conversion luminescence of the marker.

DETAILED DESCRIPTION OF THE EMBODIMENTS

The present invention will be described in detail below with reference to the accompanying drawings.

Example 1

Figure 1:
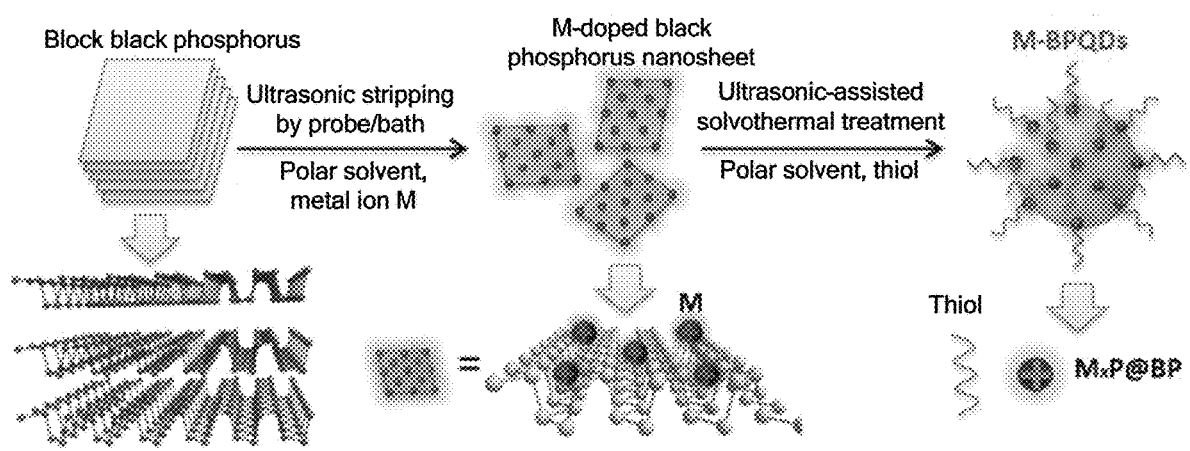
FIG. 1 is a schematic diagram of the preparation process and principle of metal ion doped black phosphorus quantum dots (M-BPQDs)
Figure 2:
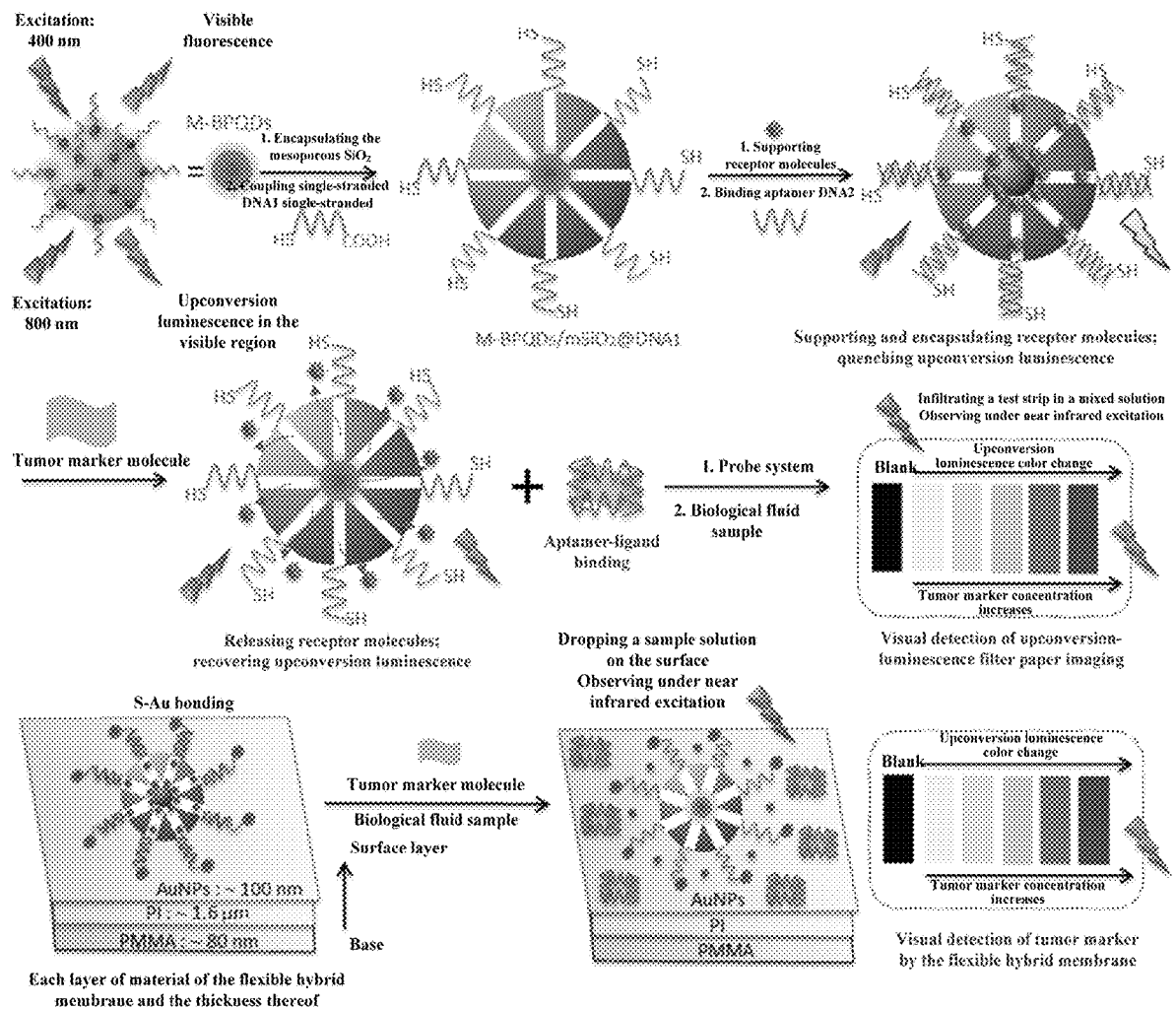
FIG. 2 is a schematic diagram of the preparation process of upconversion-luminescence flexible hybrid membrane based on M-BPQDs and its principle for visual detection of tumor markers.

The present invention relates to a method for preparing an upconversion-luminescence flexible hybrid membrane for visual detection of tumor markers. The preparation process and detection principle thereof are shown in FIGS. 1 and 2, and the specific preparation steps are as follows:

Block black phosphorus crystal was ground into a powder, mixed with N-methylpyrrolidone (NMP) in which silver nitrate was dissolved. Black phosphorus nanosheets were ultrasonically stripped by a probe and a bath, and the mercaptopropionic acid ligand was added to prepare Ag-BPQDs with an average size of 2 nm by ultrasonic-assisted solvothermal treatment. According to the Stöber method, 50 nm thick mSiO$_2$ was grown on the surface of Ag-BPQDs, then functionalized by —NH$_2$ to obtain Ag-BPQDs/mSiO$_2$—NH$_2$, and bound to single-stranded DNA1 (HS-DNA1-COOH) by carboxy-amine coupling to prepare Ag-BPQDs/mSiO$_2$@DNA1. 5-fluorouracil (5FU) entered the pores of mSiO$_2$ to complete the molecular loading of the receptor, and specific aptamer single-stranded DNA2 were added to form a double helix structure with the DNA1 to encapsulate the receptor molecule by complementary base pairing, and a nano-hybrid carrier probe Ag-BPQDs/mSiO$_2$@DNA1-DNA2@5FU was prepared. PMMA was used as a layered substrate measuring 80 nm, and the surface thereof was bonded with a layer of 1.6 μm PI, and an electrode clip fixed PMAA-PI film was immersed in an electrolyte. Using a KCl saturated calomel electrode as a reference electrode, a platinum wire electrode as an auxiliary electrode, and the PMMA-PI film as the working electrode, 10 mM HAuCl$_4$ was added to the electrolyte, and cyclic voltammetry was performed for 50 cycles to electrochemically deposit gold on the surface of the film. The nanoparticle AuNPs have a layer thickness of 50 nm, and finally a PMMA-PI-AuNPs composite film is obtained. DNA1 (HS-DNA1-COOH) tail-SH on the probe and AuNPs on the membrane were bonded by Au—S bond, and the film and the probe were connected together to form a flexible hybrid membrane. When a human serum sample contains carcinoembryonic antigen (CEA), a trace amount of sample is added dropwise to the hybrid membrane, and under the excitation of 800 nm and 5 mW near-infrared light, changes in intensity of orange-red upconversion luminescence were observed at 550 nm of the visible region of the infiltrated hybrid membrane. As the concentration of CEA in the sample increased from 10 nM to 10 μM, the up-conversion luminescence of Ag-BPQDs was gradually enhanced, and the up-conversion luminescence of the tumor marker CEA in human serum samples was visualized.

Example 2

Block black phosphorus crystal was ground into a powder, mixed with NMP in which nickel nitrate was dissolved, black phosphorus nanosheets were ultrasonically stripped by a probe and a bath, and the mercaptopropionic acid ligand was added to prepare Ni-BPQDs with an average size of 3 nm by ultrasonic-assisted solvothermal treatment. According to the Stöber method, 100 nm thick $mSiO_2$ was grown on the surface of Ni-BPQDs, then functionalized by —$NH_2$ to obtain Ni-BPQDs/$mSiO_2$—$NH_2$, and bound to single-stranded DNA1 (HS-DNA1-COOH) by carboxy-amine coupling to prepare Ni-BPQDs/$mSiO_2$@DNA1. Dopamine (DA) entered the pores of $mSiO_2$ to complete the molecular loading of the receptor, and specific aptamer single-stranded DNA2 were added to form a double helix structure with the DNA1 encapsulated receptor molecule by complementary base pairing, and a nano-hybrid carrier probe Ni-BPQDs/$mSiO_2$@DNA1-DNA2@DA was prepared. PMMA was used as a layered substrate measuring 50 nm, and the surface thereof was bonded with a layer of 1.5 μm PI, and an electrode clip fixed PMAA-PI film was immersed in an electrolyte. Using a KCl saturated calomel electrode as a reference electrode, a platinum wire electrode as an auxiliary electrode, and the PMAA-PI film as the working electrode, 10 mM $HAuCl_4$ was added to the electrolyte, and cyclic voltammetry was performed for 50 cycles to electrochemically deposit gold on the surface of the film. The nano-particle AuNPs have a layer thickness of 40 nm, and finally a PMMA-PI-AuNPs composite film is obtained. DNA1 (HS-DNA1-COOH) tail-SH on the probe and AuNPs on the membrane were bonded by Au—S bond, and the film and the probe were connected together to form a flexible hybrid membrane. When a human urine sample contains alpha-fetoprotein (AFP), a trace amount of sample is added dropwise to the hybrid membrane, and under the excitation of 800 nm and 5 mW near-infrared light, changes in intensity of orange-red upconversion luminescence were observed at 540 nm of the visible region of the infiltrated hybrid membrane. As the concentration of AFP in the sample increased from 10 nM to 100 μM, the up-conversion luminescence of Ni-BPQDs was gradually enhanced, and the up-conversion luminescence of the tumor marker AFP in human urine samples was visualized.

Example 3

Block black phosphorus crystal was ground into a powder, mixed with NMP in which cobalt nitrate was dissolved, black phosphorus nanosheets were ultrasonically stripped by a probe and a bath, and the mercaptopropionic acid ligand was added to prepare Co-BPQDs with an average size of 5 nm by ultrasonic-assisted solvothermal treatment. According to the Stöber method, 150 nm thick $mSiO_2$ was grown on the surface of Co-BPQDs, then functionalized by —$NH_2$ to obtain Co-BPQDs/$mSiO_2$—$NH_2$, and bound to single-stranded DNA1 (HS-DNA1-COOH) by carboxy-amine coupling to prepare Co-BPQDs/$mSiO_2$@DNA1. Rutin (LU) entered the pores of $mSiO_2$ to complete the molecular loading of the receptor, and specific aptamer single-stranded DNA2 were added to form a double helix structure with the DNA1 to execute the encapsulation of the receptor molecule by complementary base pairing, and a nano-hybrid carrier probe Co-BPQDs/$mSiO_2$@DNA1-DNA2@LU was prepared. PMMA was used as a layered substrate measuring 60 nm, and the surface thereof was bonded with a layer of 1.8 μm PI, and an electrode clip fixed PMAA-PI film was immersed in an electrolyte. Using a KCl saturated calomel electrode as a reference electrode, a platinum wire electrode as an auxiliary electrode, and the PMAA-PI film as the working electrode, 10 mM $HAuCl_4$ was added to the electrolyte, and cyclic voltammetry was performed for 50 cycles to electrochemically deposit gold on the surface of the film. The nano-particle AuNPs have a layer thickness of 20 nm, and finally a PMMA-PI-AuNPs composite film is obtained. DNA1 (HS-DNA1-COOH) tail-SH on the probe and AuNPs on the membrane were bonded by Au—S bond, and the film and the probe were connected together to form a flexible hybrid membrane. When a human urine sample contains prostate-specific antigen (PSA), a trace amount of sample is added dropwise to the hybrid membrane, and under the excitation of 800 nm and 5 mW near-infrared light, changes in intensity of orange-red upconversion luminescence were observed at 575 nm of the visible region of the infiltrated hybrid membrane. As the concentration of PSA in the sample increased from 10 nM to 1 mM, the up-conversion luminescence of Co-BPQDs was gradually enhanced, and the up-conversion luminescence of the tumor marker PSA in human urine samples was visualized.

The foregoing descriptions are merely preferred examples of the present invention; it should be noted that several variations and modifications can be made by those skilled in the art without departing from the principles of the present invention and should also be construed as within the scope of claims of the present invention.

What is claimed is:

1. A method for preparing an upconversion-luminescence flexible hybrid membrane for a visual detection of a tumor marker, comprising the following steps:
   (1) grinding a block black phosphorus crystal into powder, adding the powder to a polar solvent to obtain a first mixture, wherein a metal salt is dissolved in the polar solvent, ultrasonically stripping black phosphorus nanosheets from the first mixture by a probe and a bath, adding a thiol ligand to the black phosphorus nanosheets to obtain a second mixture, and preparing metal ion doped black phosphorus quantum dots (M-BPQDs) from the second mixture by an ultrasonic-assisted solvothermal treatment;
   (2) growing mesoporous silica ($mSiO_2$) on surfaces of the M-BPQDs according to a Stöber method to obtain a third mixture, conducting an amination modification to introduce a —$NH_2$ modification on the third mixture to prepare M-BPQDs/$mSiO_2$—$NH_2$, and binding the M-BPQDs/$mSiO_2$—$NH_2$ to a single-stranded DNA1 of the formula HS-DNA1-COOH by a carboxy-amine coupling to prepare M-BPQDs/$mSiO_2$@DNA1;
   (3) allowing a receptor molecule to enter a pore of the $mSiO_2$ to complete a loading of the receptor molecule, adding a specific aptamer single-stranded DNA2 for a complementary base pairing with the single-stranded DNA1 to form a double helix structure, and encapsulating the receptor molecule to obtain a nano-hybrid carrier probe M-BPQDs/$mSiO_2$@DNA1-DNA2@receptor, wherein the receptor in the nano-hybrid carrier probe M-BPQDs/$mSiO_2$@DNA1-DNA2@receptor is the receptor molecule, and the receptor molecule is 5-fluorouracil, and the receptor molecule is encapsulated in a pore of the $mSiO_2$;

(4) using polymethyl methacrylate (PMMA) as a layered substrate, bonding a layer of polyimide (PI) on a surface of a PMMA layer to obtain a PMAA-PI film, using an electrode clip to fix the PMAA-PI film to obtain an electrode clip fixed PMAA-PI film and immersing the electrode clip fixed PMAA-PI film in an electrolyte; using a KCl saturated calomel electrode as a reference electrode, a platinum wire electrode as an auxiliary electrode, and the PMMA-PI film as a working electrode, adding $HAuCl_4$ to the electrolyte, scanning the reference electrode, the auxiliary electrode and the working electrode by cyclic voltammetry, and electrochemically reducing a surface of the PMAA-PI film to form a layer of gold nanoparticles (AuNPs) to prepare a PMMA-PI-AuNPs composite film; and (5) bonding the terminal sulfhydryl group of the single-stranded DNA1 on the nano-hybrid carrier probe to the AuNPs on the PMMA-PI-AuNPs composite film by Au—S bonds, and connecting the PMMA-PI-AuNPs composite film and the nano-hybrid carrier probe together to construct the upconversion-luminescence flexible hybrid membrane.

2. The method according to claim 1, wherein the metal ion in step (1) is $Ag+$, $Mn^{2+}$, $Co^{2+}$, or $Ni^{2+}$; and the M-BPQDs are 1-5 nm in size.

3. The method according to claim 1, wherein a thickness of the $mSiO_2$ on the surfaces of the M-BPQDs in step (2) is 50-200 nm.

4. The method according to claim 1, wherein the specific aptamer single-stranded DNA2 is a single-stranded DNA aptamer specifically binding to the tumor marker, wherein the tumor marker is carcinoembryonic antigen (CEA), alpha-fetoprotein (AFP), carbohydrate antigen (CA), or prostate specific antigen (PSA).

5. The method according to claim 1, wherein in step (4), a thickness of the PMMA layer is 50-100 nm, a thickness of the layer of PI is 1-2 μm, and a thickness of the layer of AuNPs is 10-100 nm.

6. A method for preparing an upconversion-luminescence flexible hybrid membrane for a visual detection of a tumor marker, comprising the following steps:

(1) grinding a block black phosphorus crystal into powder, adding the powder to a polar solvent to obtain a first mixture, wherein a metal salt is dissolved in the polar solvent, ultrasonically stripping black phosphorus nanosheets from the first mixture by a probe and a bath, adding a thiol ligand to the black phosphorus nanosheets to obtain a second mixture, and preparing metal ion doped black phosphorus quantum dots (M-BPQDs) from the second mixture by an ultrasonic-assisted solvothermal treatment;

(2) growing mesoporous silica ($mSiO_2$) on surfaces of the M-BPQDs according to a Stöber method to obtain a third mixture, conducting an amination modification to introduce a —$NH_2$ modification on the third mixture to prepare M-BPQDs/$mSiO_2$—$NH_2$, and binding the M-BPQDs/$mSiO_2$—$NH_2$ to a single-stranded DNA1 of the formula HS-DNA1-COOH by a carboxy-amine coupling to prepare M-BPQDs/$mSiO_2$@DNA1;

(3) allowing a receptor molecule to enter a pore of the $mSiO_2$ to complete a loading of the receptor molecule, adding a specific aptamer single-stranded DNA2 for a complementary base pairing with the single-stranded DNA1 to form a double helix structure, and encapsulating the receptor molecule to obtain a nano-hybrid carrier probe M-BPQDs/$mSiO_2$@DNA1-DNA2@receptor, wherein the receptor in the nano-hybrid carrier probe M-BPQDs/$mSiO_2$@DNA1-DNA2@receptor is the receptor molecule, and the receptor molecule is dopamine, and the receptor molecule is encapsulated in a pore of the $mSiO_2$;

(4) using polymethyl methacrylate (PMMA) as a layered substrate, bonding a layer of polyimide (PI) on a surface of a PMMA layer to obtain a PMAA-PI film, using an electrode clip to fix the PMAA-PI film to obtain an electrode clip fixed PMAA-PI film and immersing the electrode clip fixed PMAA-PI film in an electrolyte; using a KCl saturated calomel electrode as a reference electrode, a platinum wire electrode as an auxiliary electrode, and the PMMA-PI film as a working electrode, adding $HAuCl_4$ to the electrolyte, scanning the reference electrode, the auxiliary electrode and the working electrode by cyclic voltammetry, and electrochemically reducing a surface of the PMAA-PI film to form a layer of gold nanoparticles (AuNPs) to prepare a PMMA-PI-AuNPs composite film; and (5) bonding the terminal sulfhydryl group of the single-stranded DNA1 on the nano-hybrid carrier probe to the AuNPs on the PMMA-PI-AuNPs composite film by Au—S bonds, and connecting the PMMA-PI-AuNPs composite film and the nano-hybrid carrier probe together to construct the upconversion-luminescence flexible hybrid membrane.

7. The method according to claim 6, wherein the metal ion in step (1) is $Ag^+$, $Mn^{2+}$, $Co^{2+}$, or $Ni^{2+}$; and the M-BPQDs are 1-5 nm in size.

8. The method according to claim 6, wherein a thickness of the $mSiO_2$ on the surfaces of the M-BPQDs in step (2) is 50-200 nm.

9. The method according to claim 6, wherein the specific aptamer single-stranded DNA2 is a single-stranded DNA aptamer specifically binding to the tumor marker, wherein the tumor marker is carcinoembryonic antigen (CEA), alpha-fetoprotein (AFP), carbohydrate antigen (CA), or prostate specific antigen (PSA).

10. The method according to claim 6, wherein in step (4), a thickness of the PMMA layer is 50-100 nm, a thickness of the layer of PI is 1-2 μm, and a thickness of the layer of AuNPs is 10-100 nm.

11. A method for preparing an upconversion-luminescence flexible hybrid membrane for a visual detection of a tumor marker, comprising the following steps:

(1) grinding a block black phosphorus crystal into powder, adding the powder to a polar solvent to obtain a first mixture, wherein a metal salt is dissolved in the polar solvent, ultrasonically stripping black phosphorus nanosheets from the first mixture by a probe and a bath, adding a thiol ligand to the black phosphorus nanosheets to obtain a second mixture, and preparing metal ion doped black phosphorus quantum dots (M-BPQDs) from the second mixture by an ultrasonic-assisted solvothermal treatment;

(2) growing mesoporous silica ($mSiO_2$) on surfaces of the M-BPQDs according to a Stöber method to obtain a third mixture, conducting an amination modification to introduce a —$NH_2$ modification on the third mixture to prepare M-BPQDs/$mSiO_2$—$NH_2$, and binding the M-BPQDs/$mSiO_2$—$NH_2$ to a single-stranded DNA1 of the formula HS-DNA1-COOH by a carboxy-amine coupling to prepare M-BPQDs/$mSiO_2$@DNA1;

(3) allowing a receptor molecule to enter a pore of the $mSiO_2$ to complete a loading of the receptor molecule, adding a specific aptamer single-stranded DNA2 for a complementary base pairing with the single-stranded DNA1 to form a double helix structure, and encapsulating the receptor molecule to obtain a nano-hybrid carrier probe M-BPQDs/mSiO$_2$@DNA1-DNA2@receptor, wherein the receptor in the nano-hybrid carrier probe M-BPQDs/mSiO$_2$@DNA1-DNA2@receptor is the receptor molecule, and the receptor molecule is rutin, and the receptor molecule is encapsulated in a pore of the mSiO$_2$;

(4) using polymethyl methacrylate (PMMA) as a layered substrate, bonding a layer of polyimide (PI) on a surface of a PMMA layer to obtain a PMAA-PI film, using an electrode clip to fix the PMAA-PI film to obtain an electrode clip fixed PMAA-PI film and immersing the electrode clip fixed PMAA-PI film in an electrolyte; using a KCl saturated calomel electrode as a reference electrode, a platinum wire electrode as an auxiliary electrode, and the PMMA-PI film as a working electrode, adding HAuCl$_4$ to the electrolyte, scanning the reference electrode, the auxiliary electrode and the working electrode by cyclic voltammetry, and electrochemically reducing a surface of the PMAA-PI film to form a layer of gold nanoparticles (AuNPs) to prepare a PMMA-PI-AuNPs composite film; and (5) bonding the terminal sulfhydryl group of the single-stranded DNA1 on the nano-hybrid carrier probe to the AuNPs on the PMMA-PI-AuNPs composite film by Au—S bonds, and connecting the PMMA-PI-AuNPs composite film and the nano-hybrid carrier probe together to construct the upconversion-luminescence flexible hybrid membrane.

12. The method according to claim 11, wherein the metal ion in step (1) is $Ag^+$, $Mn^{2+}$, $Co^{2+}$, or $Ni^{2+}$; and the M-BPQDs are 1-5 nm in size.

13. The method according to claim 11, wherein a thickness of the mSiO$_2$ on the surfaces of the M-BPQDs in step (2) is 50-200 nm.

14. The method according to claim 11, wherein the specific aptamer single-stranded DNA2 is a single-stranded DNA aptamer specifically binding to the tumor marker, wherein the tumor marker is carcinoembryonic antigen (CEA), alpha-fetoprotein (AFP), carbohydrate antigen (CA), or prostate specific antigen (PSA).

15. The method according to claim 11, wherein in step (4), a thickness of the PMMA layer is 50-100 nm, a thickness of the layer of PI is 1-2 μm, and a thickness of the layer of AuNPs is 10-100 nm.

* * * * *